United States Patent [19]
Pfirrmann

[11] Patent Number: 5,972,933
[45] Date of Patent: Oct. 26, 1999

[54] METHOD OF TREATING MICROBIAL INFECTIONS

[75] Inventor: Rolf W. Pfirrmann, Lucerne, Switzerland

[73] Assignee: Ed. Geistlich Söhne AG Für Chemische Industrie, Switzerland

[21] Appl. No.: 09/004,063

[22] Filed: Jan. 8, 1998

[51] Int. Cl.$^6$ ............ A61K 31/54; A01N 43/36; A01N 43/56; A01N 43/32

[52] U.S. Cl. ............ 514/222.5; 514/422; 424/400; 424/404; 424/408; 424/434

[58] Field of Search ............ 514/222.5, 422; 424/404, 400, 408, 409, 436

[56] References Cited

U.S. PATENT DOCUMENTS

| | | |
|---|---|---|
| 3,423,408 | 1/1969 | Pfirrmann . |
| 4,002,889 | 1/1977 | Bannister et al. .................. 424/181 |
| 4,096,241 | 6/1978 | Geistlich et al. . |
| 4,107,305 | 8/1978 | Pfirrmann . |
| 4,337,251 | 6/1982 | Pfirrmann . |
| 4,587,268 | 5/1986 | Pfirrmann . |
| 4,604,391 | 8/1986 | Pfirrmann . |
| 4,626,536 | 12/1986 | Pfirrmann . |
| 4,772,468 | 9/1988 | Pfirrmann . |
| 4,882,149 | 11/1989 | Spector .......................... 424/425 |
| 4,960,415 | 10/1990 | Reinmüller . |
| 5,077,281 | 12/1991 | Reinmiiller ....................... 514/56 |
| 5,187,082 | 2/1993 | Hamill et al. ................... 435/71.3 |
| 5,210,083 | 5/1993 | Pfirrmann . |
| 5,304,540 | 4/1994 | Blackburn et al. .................. 514/2 |
| 5,417,975 | 5/1995 | Lussi et al. ..................... 424/423 |
| 5,559,096 | 9/1996 | Edwards et al. ................... 514/12 |
| 5,591,714 | 1/1997 | Nagarajan et al. .................. 514/9 |
| 5,593,665 | 1/1997 | Pfirrmann et al. . |
| 5,650,320 | 7/1997 | Caufield et al. ................. 435/252.3 |

FOREIGN PATENT DOCUMENTS

| | | |
|---|---|---|
| 9006138 | 6/1990 | WIPO . |

OTHER PUBLICATIONS

Jean–Louis Vincent, Dear SIRS, I'm sorry to say that I don't like you . . . , Another Point of View, Crit Care Med. 1997, vol. 25, No. 2, pp. 372–374.
R.C. Bone, Sepsis and Septic Shock, Consultant Series In Infectious Disease (3), No. 2, pp. 1–25.
Stephen C. Stinson, Drug Firms Restock Antibacterial Arsenal, Product Report, Sep. 23, 1996, C&EN.
U. Rampp, Medizin Im Dialog, Aug. 1996 (untranslated).
Traub et al. Chemotherapy 39 (4): 254–264, 1993.
Browne et al. Surg. Gynecol. Obstetr. 145: 84–846, 1977.
Willatts et al. Critic Care Med. 23: 1033–1039, 1995.
Jones et al. J. Appl. Bacteriol. 71: 218–27, 1991.
Anon. Drugs of the Future 14 (3): 237–238, 1989.
Reith. Langenbecks Archiv. Fuer Chirurgie 382 (4 Suppl. 1) S14–S17, abstract, 1997.
Krawzak et al. Aktuel. Chir. 22/1 : 19–22, abstract, 1987.
K Tarao et al. J. Clin. Gastroenterol. 4(3): 263–267, 1982.
WH Traub et al. Chemotherapy 39/5: 322–330, 1993.
REW Hancock. Lancet 349: 418–422, 1997.
KK Lai et al. 35th Interscience Conference on Antimicrobial Agents and Chemotherapy, Sep. 17–20, 1995. San Francisco, USA. Abstr. No. J71, p. 270.
M Zimmermann et al. Arzneim–Forsch/Drug Res. 42(II), 9: 1157–1159, 1985.
Focht et al., "spectrum of pathogens and resistance in peritonitis", Langenbecks Archiv Für Chirurgie, vol.382, No. 4, 1997, pp. s1–s4.
Vankemmel et al., "Traitement anti–infectieux local et général par utilisation d'un nouvel antiseptique en chirurgie bilio–pancréatique: un défi aux antibiotiques", Med Interne, vol. 14, No. 12, 1979, pp. 683–688 (untranslated).
Ruegsegger et al., "tauroline in intra–abdominal infections", Helv. Chir. Acta, vol. 45, No. 6, 1979, pp. 743–747 (untranslated).
Ruegsegger et al., "Comparative study on prophylactic antibiotics versus perioperative taurolidine in colonic surgery", Helvetica Chirur Acta, vol. 50, No. 1–2, 1983, pp. 117–120 (untranslated).
Rosman et al., "effect of intraperitoneal antimicrobials on the concentration of bacteria, endotoxin and TNF in abdominal fluid and plasma in rats", Eur. Surg. Res., vol. 28, No. 5, 1996, pp. 351–360.
Gortz, G., "Local antiseptic and antiendotoxic measures in the case of intraabdominal infections", Langenbecks Archiv Für Chirurgie, vol. 382, No. 4, 1997, pp. s37–s41.
Linder et al., "Therapy of purulent peritonitis", Langenbecks Arch Chir, vol. 353, No. 4, 1981, pp. 241–250.
Browne, M.K., "The treatment of peritonitis by an antiseptic taurolin", Pharmatherapeutica, vol. 2, No. 8, 1981, pp. 517–522.

*Primary Examiner*—James C. Housel
*Assistant Examiner*—S. Devi
*Attorney, Agent, or Firm*—Rothwell, Figg, Ernst & Kurz, p.c.

[57] ABSTRACT

A method and composition for treatment of a microbial infection of a patient involves introduction into the gut of a patient an antimicrobial amount of an antimicrobial medicament which is cell wall constituent-inactivating, endotoxin non-releasing, exotoxin-inactivating or a combination thereof.

18 Claims, No Drawings

METHOD OF TREATING MICROBIAL INFECTIONS

BACKGROUND OF THE INVENTION

1. Field of the Invention

The present invention relates to the field of treating patients having microbial infections.

2. Description of the Background Art

The broad use of antibiotics significantly influences multi-resistance of microorganisms, and has greatly increased the number of antibiotic-resistant microorganisms.

Antibiotic-resistant strains of Enterococci such as vancomycin-resistant strains of *Enterococcus faecium* and *Enterococcus faecalis* (VRE), as well as antibiotic-resistant strains of Staphylococci such as methicillin-resistant *Staphylococcus aureus* (MRSA) can cause severe nosocomial infections and diarrhea. Common nosocomial infections in intensive care units are pneumonia, urinary tract infections, septicemia, catheter-sepsis and postoperative wound infections.

Antibiotic-resistant microorganisms are increasingly associated with severe morbidity and mortality among hospitalized patients, particularly among patients with VRE colonizations in long-term care facilities and in those returning to community care, which now present a major public health threat.

Management of life-threatening infections caused by antibiotic-resistant strains is particularly difficult, as the range of therapeutic options is very limited. There is a rapid increase in incidences of nosocomial infection and colonization with vancomycin-resistant Enterococci (VRE) throughout the whole world. Treatment options presently are combinations of antibiotics or experimental substances with uncertain efficacy. The potential emergence of vancomycin resistance in clinical isolates of *S. aureus* is dangerous. Successful prevention is necessary to prevent person-to-person transmission of VRE.

The compounds Taurolidine (Taurolin®) and Taurultam are known antimicrobial substances with broad-spectrum activity against aerobic and anaerobic bacteria, mycobacteria and fungi. Unlike antibiotics, these compounds do not result in release of large quantities of bacterial toxins. They have been suggested as a substitute for antibiotics for administration in patients locally, by injection or by infusion, to combat infections of the teeth and jaw, wound infections, osteitis, endotoxaemia, peritonitis, sepsis and septic shock. However, it is known that these compounds have a short half-life in vivo and they never have been suggested for treatment of infections of the gut.

There remains an urgent need in the art for improved methods of treating patients with microbial antibiotic-multiresistant infections, including gut infections.

SUMMARY OF THE INVENTION

In accordance with the present invention, a method of treating a microbial infection of a patient comprises introducing into the gut of the patient an antimicrobial amount of an antimicrobial medicament selected from the group consisting of antimicrobial medicaments which are cell wall constituent-inactivating, endotoxin non-releasing, exotoxin-inactivating, and combinations thereof, so as to treat the microbial gut infection of the patient.

DETAILED DESCRIPTION OF THE PREFERRED EMBODIMENTS

As used herein, the term "patient" refers to a mammalian patient, preferably a human patient with microbial infection of the gut.

The antimicrobial compounds utilized in accordance with the invention are cell wall constituent-inactivating, endotoxin non-releasing, and/or exotoxin inactivating antimicrobial compounds, which are slow-acting bactericides. Preferably, the compounds are cell wall-crosslinking compounds such as Taurolidine and Taurultam. Taurolidine is a unique antimicrobial agent having an exceptionally broad spectrum of antimicrobial and antibacterial activity including activity against gram positive and gram negative, aerobic, and anaerobic bacteria. Resistance has not been observed either in vivo or in vitro. Additionally, the compound posesses useful activity against most yeast-like and filamentous fungi.

The compounds Taurolidine and Taurultam are as disclosed in U.S. Pat. No. 5,210,083, incorporated herein by reference.

The antimicrobial compounds utilized in the present invention are distinguished from conventional antibiotics as ordinarily understood in the art, i.e., antibiotics that act by attacking, breaking and/or rupturing microbial cell walls (disturbance of murein-biosynthesis, protein-biosynthesis, DNA topology, etc.), resulting in release of microbial toxins from the microbial cells.

While the invention is further described with respect to Taurolidine and Taurultam, the invention also is applicable to use of other cell wall constituent-inactivating, antimicrobial compounds which release no or substantially insignificant toxins. Thus, the invention is applicable to Taurolidine, Taurultam, and antimicrobial medicaments which act in a substantially similar manner.

As indicated above, the present invention is directed to a method of treating a patient with microbial infection, such as bacterial and/or fungal gut infection.

According to one aspect, the invention is applicable to a method of treating a microbial digestive tract infection of a patient, comprising introducing into digestive tract of the patient a non-antibiotic, antimicrobial medicament effective against antibiotic-resistant microbes.

The invention is particularly applicable to microbial infections of the digestive tract, intestinal tract or gut, and is advantageous for use against infections of the gut by antibiotic-resistant microorganisms such as antibiotic-resistant strains of gram negative or gram positive bacteria, antibiotic-resistant and multi-resistant strains of Enterococci, antibiotic-resistant and multi-resistant strains of Staphylococci, *Enterococcus faecalis*, *Enterococcus facium*, *Staphylococcus aureus*, vancomycin-resistant *Enterococcus faecalis* (VRE) strains, and methicillin-resistant *Staphylococcus aureus* (MRSA) strains.

The antimicrobial medicament can be administered as a tablet, capsule, liquid, suspension, suppository or the like, preferrably as enteric coated tablets and capsules, ensuring biological availability, controlling the effects of the drug, and avoiding side effects.

In preferred embodiments, the antimicrobial medicament is administered enterally. One suitable method of administration is oral administration. For treatment of microbial infections of the lower bowel or colon, administration can be orally and/or rectally. Further embodiments may include injection and/or intravenous administration of the antimicrobial medicament either alone, or in conjunction with oral and/or rectal administration.

In particularly preferred embodiments, the antimicrobial medicament is administered so that the medicament is substantially continuously present in the patient's gut over the course of the treatment, so as to inhibit microbial proliferation and/or reproduction in the patient's gut. Enteric coating soft or hard gelatin capsules can be utilized to stabilize acid sensitivity, improve tolerance and avoid gastric lesions, gastric disorders, and irritation of the gastric mucosa after peroral administration. Enteric coating delays onset of action, and targets release in the small intestine.

The invention also is applicable to pharmaceutical compositions for treatment of microbial infections. Particularly preferred pharmaceutical compositions in accordance with the present invention, for treatment of microbial gut infections, include an antimicrobial amount of an antimicrobial medicament selected from the group consisting of antimicrobial medicaments which are cell wall constituent-inactivating, endotoxin non-releasing, exotoxin-inactivating, and combinations thereof, in a formulation selected from the group consisting of (1) delayed release formulations including a pharmaceutically acceptable delayed release excipient operatively associated with the antimicrobial medicament, which delays release of the medicament when administered orally until entry into a patient's intestinal tract, and (2) sustained release formulations including a pharmaceutically acceptable sustained release excipient operatively associated with the medicament so as to substantially continuously release the medicament after entry into a patient's intestinal tract. In particularly preferred sustained release formulations, the medicament is substantially continuously released after entry into a patient's intestinal tract for a period of at least one hour, more preferably at least 2, 3, 4, 5, 6, 7, 8 hours or longer.

Sustained and delayed release formulations can be made with:

1) Use of various matrices to control drug release, such matrices including various polymers (U.S. Pat. Nos. 5,618,559, 5,637,320, 5,648,096, 5,654,005), cellulosic materials (U.S. Pat. Nos. 5,607,695, 5,609,884, 5,624,683, 5,656,295) fatty acids and polyglycerols (U.S. Pat. Nos. 5,593,690, 5,602,180, 5,628,993), polysacharides (U.S. Pat. No. 5,629,018) and gelatin derivatives (U.S. Pat. No. 5,614,219).

2) Use of gastroresistant coatings including polymeric and vinylic coatings (U.S. Pat. Nos. 5,639,476, 5,637,320, 5,616,345, 5,603,957, 5,656,291, 5,614,218, 5,541,171, 5,541,170), and cellulosic coatings (U.S. Pat. Nos. 5,510,114, 5,603,957).

3) Use of additives to the active ingredients that prolong release, such as fatty acids (U.S. Pat. No. 5,597,562).

U.S. Pat. No. 5,650,170 discloses dosage forms for delivering drugs at a controlled rate to the intestine and to the colon.

All of the above-cited U.S. Patents are incorporated herein by reference.

In preferred embodiments, the antimicrobial medicament is administered to the patient substantially continuously for a time period of about 5 to 10 days so as to substantially eliminate the microbial infection in the patient. Taurolin in vitro has proven to be effective against all gram negative and gram positive bacterial strains tested to-date, including antibiotic multi-resistant strains such as *Enterococcus faecalis* and *Enterococcus facium*, VRE and MRSA.

Enterococci are widely distributed in nature and mainly colonized the colon. Normally, Enterococci are not pathogenous. However, due to abuse of antibiotics such as vancomycin, as well as antibiotic additives in animal feed, multi-resistant bacterial strains can be isolated as concurrent flora in infections of urinary passages, gall bladder infections and wound infections.

A most dangerous form of Enterococcus infection is endocarditis. Chronic diarrhea also is caused by such infection. VREs are especially dangerous as they can pass on their resistance to other bacterial strains such as *Staphylococcus aureus* or *Staphylococcus epidermidis*.

VREs can infect the gut and cause severe diarrhea. This can be treated in accordance with the present invention by oral administration of the antimicrobial medicament, but if sepsis is also present in the patient, concurrent intravenous administration of the antimicrobial medicament as a 2% sterile solution may be desirable.

MRSA infection may be treatable by intravenous administration of the antimicrobial medicament alone, but if the patient is experiencing severe diarrhea, both oral and intravenous administration may be desirable. MRSA can infect the skin and mucous membranes of patients, can be present in a patient's urine, and is easily transmitted to other persons. Additionally, MRSA-infected patients sometimes have meningitis.

Taurolidine and/or Taurultam may be administered in an aqueous solution at a concentration of about 0.1–3% (e.g., 0.5%) by weight Taurolidine and/or Taurultam. Suitable compositions are disclosed in the previously mentioned U.S. Pat. No. 5,210,083. Aqueous solutions of Taurolidine and/or Taurultam may be administered during the treatment period in a total amount of about 0.5–5 liters (which may correspond to 1 liter/2% per day, 20–30 gms/24 hours/adult human patient of Taurolidine).

Treatment of severe microbial gut infections in accordance with the present invention can save the lives of many patients, as compared to conventional treatments. Taurolidine and Taurultam destroy bacteria slowly, cross-linking the bacterial cell walls and thereby preventing the release of bacterial toxins. The cross-linking of the bacterial cell walls inactivates the bacterial toxins which could otherwise be highly poisonous. Additionally, because of this unique mode of action with bacterial cell walls, no resistance development by microbes has been observed.

Taurolidine and/or Taurultam prevent over-production of cytokines in the patient by monocytes of the blood. While addition of antibiotics to human blood leads to a rise in TNF-a, the addition of Taurolidine and/or Taurultam to antibiotic-treated cultures prevents a rise in TNF production as a result of nearly complete neutralization of released endotoxins.

While classic antibiotics act quickly, Taurolidine and/or Taurultam kills bacteria slowly. Furthermore the bacteremia disappears slowly while treatment with Taurolidine and/or Taurultam continues over a period of time. Bacterial toxins are prevented from release, and no over-production of cytokines occurs.

The invention is illustrated by the following Examples, which are not intended to be limiting.

EXAMPLE 1

Capsules

| 1. Soft-gelatin capsules, System Scherer ™/Size 16 oblong | | |
|---|---|---|
| Content: | 500 mg | Taurolidine (crystalline) Migliol ™ (medium chain triglyceride) Softisan 367 ™ hard fat |
| | 600 mg | (Caprylic, capric, stearic triglyceride) |
| Total filling weight | 1100 mg. | |

-continued

2. Hard-gelatin capsules
   Qualicap ™ Lilly transparent/size 0

Contents:    300 mg   Taurolidine (crystalline)
                  6 mg   Talc, Acrosil ™, Mg-stearate
                         8:1:1(additive)
                ——————
                306 mg

EXAMPLE 2

Tablets

| | Substance | Amount mg/Tablet |
|---|---|---|
| 1. | Taurolidine or Taurultam | 300 |
|  | Emdex ™ (Dextrates*) | 200 |
|  | direct compression Dextrate | |
|  | Magnesium stearate | 10 |
| 2. | Taurolidine or Taurultum | 300 |
|  | Methacell ™ K4M premium | 200 |
|  | (Hydroxypropyl methylcellulose) | |
|  | Corn Starch | 12 |
|  | Magnesium stearate | 10 |
|  | Gastric juice-resistant | |
|  | Endragit ™ RS 100 and dibutylphthalate | |
|  | in methanol (7.2 parts and 0.8 parts) | |
| 3. | Taurolidine or Taurultam | 500 |
|  | Methocell ™ E15LV premium | 250 |
|  | Microcrystalline Cellulose | 50 |
|  | Magnesium stearate | 10 |
| 4. | Taurolidine or Taurultam | 300 |
|  | Methocell ™ E15LV premium | 200 |
|  | (Hydroxypropylmethylcellulose) | |
|  | Microcrystalline Cellulose | 50 |
|  | Talc | 16 |
|  | Magnesium stearate | 2 |
|  | Aerosil ™ 200 | 2 |
|  | gastric juice-resistant Endragit ™ | |
|  | (Polymethacrylate) | |

*Dextrates, purified mixture of saccharides resulting from the controlled enzymatic hydrolysis of starch USP/HF 23/18
Dose: 3–4 Tablets daily or more to reach desired blood level, and in severe cases, enough tablets or capsules to deliver to the patient up to 10 grams or more Taurolidine per day.

EXAMPLE 3

Taurolidine Minimum Inhibition Concentrations (MICs) for Methicillin-Resistant *Staphylococcus aureus* (MRSA) and Vancomycin-Resistant *Enterococcus faecalis* (VRE) Strains Introduction
Methicillin-Resistant *Staph. aureus* (EMRSA 15)

Because of their resistance characteristics, Staphylococci presently are the pathogens most responsible for severe nosocomial infections.

Against penicillinase resistant Betalactam-antibiotics such as methicillin, approximately 10% of the Staphylococcus strains are resistant. Methicillin-resistance is very problematic in the clinic, as it often happens that a multi-resistance develops. It can initiate invasive and difficult to treat toxin-medicated infection processes. These Staphylococci are resistant against all antibiotics, including gyrase-inhibitors with the exception of vancomycin.

Vancomycin-Resistant *Enterococcus faecalis*

In clinical practice, vancomycin-resistant strains of *Enterococcus faecalis* are on the increase.

Conclusion

Owing to its chemical mechanism of action with the bacterial cell wall, taurolidine is fully effective in vitro against pathogens which are resistant to antibiotics such as methicillin and vancomycin.

Taurolidine MICs for Methicillin-Resistant *Staphylococcus aureus* (MRSA) and Vancomycin-Resistant *Enterococcus faecalis* (VRE) Strains Test Strains All test strains were clinical isolates recovered from patients attending Hammersmith Hospital, London. Strains of *Staphylococcus aureus* (epidemic methicillin-resistant strain 15 (EMRSA 15) and vancomycin-resistant *Enterococcus faecalis* were broadly unselected isolates from local culture collections. However, strain selection was conducted so as to ensure that isolates were not consecutive isolates from individual patients.

Local EMRSA 15 strains are typically resistant in vitro to penicillins, including methicillin (cloxacillin), erythromycin, clindamycin, ciprofloxacin, aminoglycosides and mupirocin. Commonly encountered strains of VRE, designated HAM-1, show high level gentamicin resistance in addition to resistance in vitro to ampicillin, erythromycin, vancomycin, telcoplanin.

Disc Sensitivity Testing

All routine sensitivity testing was performed using a standard disc diffusion technique (Stokes) performed on Unipath (Oxoid) Diagnostic Sensitivity Test agar with 5% lysed horse blood.

Control Organisms

Testing of Staphylococci—Staphylococcus aureus (Oxford strain) NCTC 6571

Testing for Enterococci—*Enterococcus faecium* NCTC 12697

Inoculum & Test Procedure

Inocula for test and control organisms were prepared from overnight 37° C. Unipath (Oxoid) Brain Heart Infusion broth cultures. Prom these well-mixed cultures, 2 drops (t/u ml) were transferred to 3 ml sterile water. This suspension was used to moisten sterile cotton tipped swabs which were then used with a rotary plater for inoculation of test plates.

Antibiotic Discs

The following disc sets were used for sensitivity testing:

| Staphylococci | | | |
|---|---|---|---|
| Trimethoprim | 5 $\mu$g | Gentamicin | 10 $\mu$g |
| Benzyl penicillin | 1 unit | Cloxacillin | 5 $\mu$g |
| Erythromycin | 15 $\mu$g | Rifampicin | 2 $\mu$g |
| Clindamicin | 2 $\mu$g | Teicoplanin | 30 $\mu$g |
| Fucidin | 10 $\mu$g | Ciprofloxacin | 1 $\mu$g |
| Vancomycin | 30 $\mu$g | Mupirocin | 30 $\mu$g |
| Enterococci | | | |
| Ampicillin | 10 $\mu$g | | |
| Vancomycin | 30 $\mu$g | | |
| Teicoplanin | 30 $\mu$g | | |
| Gentamicin | 200 $\mu$g | | |
| Chloramphenicol | 10 $\mu$g | | |
| Erythromycin | 15 $\mu$g | | |

Methicillin Sensitivity Testing

Methicillin (cloxacillin) sensitivity for Staphylococci was confirmed using a methicillin test strips (Methi-test, Medical Wire Limited—MW981) and a heavy inoculum. This was prepared by adding 5 colonies from an overnight nutrient agar plate culture 3 ml water.

For each organism, including sensitive and resistant controls, a loop was charged with the heavy inoculum suspension and streaked across a Unipath (Oxoid) Diagnostic Sensitivity Test plus 5% lysed horse blood agar plate in a single direction. A methicillin strip was then placed on the surface of the plate at right angles to the inocula. Up to 4 test strains, plus sensitive (Oxford Staphylococcus NCTC 6571) and resistant controls are accommodated on each test plate. The plate was incubated overnight at 30° C.

Test Interpretation

Methicillin

Test zones <5 mm smaller than the control zone are SENSITIVE. Zones <5 mm smaller than the control are RESISTANT. There is no indeterminate category with methicillin.

Other Drugs

Except for methicillin tests, interpretation of results is based on the following criteria:

| | |
|---|---|
| Sensitive | test zones greater than, equal to, or no more than 3 mm smaller than the control zone |
| Resistant | test zones less than 3 mm |
| Indeterminate | test zone greater than 3 mm, but more than 3 mm less than the control zone. |

Taurolidine MICs

Taurolidine MICs were performed using a sample of authenticated anhydrous micronised taurolidine batch number E/40522/4 (Geistlich Pharma AG, Wolhusen, Switzerland).

An aqueous stock solution of taurolidine was prepared to contain 2 g/100 ml taurolidine in water. This preparation was solubilized and sterilized by heating to 121° C. (15 psi) for 15 minutes.

Using this stock solution, serial doubling dilution of taurolidine were prepared in Unipath (Oxoid) Nutrient Broth Number 2 using 50 $\mu$l volumes in sterile round bottom microdilution trays. To these dilutions was added an equal volume of drug-free broth containing a suspension of the test organism to give a final inoculumn density of approximately $10^3$ cfu. Inocula were prepared from overnight drug-free broth cultures of each test organism in Unipath (Oxoid) Nutrient Broth Number 2.

Final test concentrations of taurolidine were as follows:

| | |
|---|---|
| 2,000 mg/l | 375 mg/l |
| 1,500 mg/l | 250 mg/l |
| 1,000 mg/l | 190 mg/l |
| 750 mg/l | 125 mg/l |
| 500 mg/l | 62 mg/l |

All tests were incubated at 37 C for 18 hours. The MIC was defined as the lowest concentration of drug showing no visible evidence of growth.

Results

The results of disc sensitivity testing and taurolidine MICs are summarized below. There appears no difference in level of susceptibility to taurolidine for the strains examined when compared to the reference strain NCTC 6571 or the results from previous studies performed with fully sensitive strains.

| | TRI | PEN | ERY | CLI | FUC | VAN | GEN | CLX | RIF | TEI | CIP | MUP | AMP | CHL | Taurolidine MIC (mg/fl) |
|---|---|---|---|---|---|---|---|---|---|---|---|---|---|---|---|
| S. aureus | S | R | R | R | S | S | R | R | S | S | R | R | | | 500 |
| | S | R | R | R | S | S | R | R | S | S | R | R | | | 500 |
| | S | R | R | R | S | S | R | R | S | S | R | R | | | 500 |
| | S | R | R | R | S | S | R | R | S | S | R | R | | | 500 |
| E. faecium | | | R | | | R | R | | | R | | | R | S | 750 |
| | | | R | | | R | R | | | R | | | R | S | 375 |
| | | | R | | | R | R | | | R | | | R | S | 500 |
| | | | R | | | R | R | | | R | | | R | S | 375 |
| S. aureus NCTC 6571 | S | S | S | S | S | S | S | S | S | S | S | S | S | S | 600 |

EXAMPLE 4

Taurolidine Susceptibility of Enterococcus Species

Worldwide, vancomycin-resistant strains of *Enterococcus faecium* and *Enterococcus faecalis* (VRE) are increasingly associated with severe morbidity and mortality among hospitalized patients. Particularly difficult is the increasing incidence of colonization with VRE seen among patients in long-term-care facilities and in those returning to community care which now present a major public health threat. Management of life-threatening infections caused by these strains is particularly difficult as the range of therapeutic options is severely limited. Taurolidine (Taurolin®, Geistlich Pharma AG, Switzerland) is an antimicrobial medicament for parenteral or local administration and is characterized by broad spectrum of antimicrobial activity as well as potentially valuable cytokine-moderating (anti-endotoxic) activity.

The in vitro susceptibility to taurolidine of a panel of clinical isolates and reference strains of *Enterococcus faecium* (n=20,7 strains vancomycin resistant) and *Enterococcus faecalis* (n-53,5 strains vancomycin resistant) has been examined. There was no difference in degree of susceptibility between strains of *E faecalis* (MIC mode 375 $\mu$g/ml, range 125–500 $\mu$g/ml) and *E. faecium* (MIC mode 375 $\mu$g/ml, range 95–375 $\mu$g/ml). In all cases, the Minimum Bacteriocidal Concentration (MBC) of taurolidine was within 2 dilutions of the corresponding value for MIC confirming a bactericidal mode of action. In vitro resistance to taurolidine was not observed.

No differences were noted between the MICs or MBCs for vancomycin-sensitive or vancomycin-resistant strains of Enterococci or for strains obtained from various locations across Europe (Switzerland, Germany, UK) On the basis of these limited in vitro data, taurolidine provides a further therapeutic option for selected patients with severe or life threatening infections caused by VRE. The activity of this agent against vancomycin-resistant and vancomycin-sensitive strains of Enterococci indicates that taurolidine adds a further dimension to the limited armamentarium available against these increasingly common bacterial pathogens.

The results are shown in Table 1.

TABLE 1

E. Faecium

| (all strains) | | (VAN R strains) | | (VAN S strains) | |
| --- | --- | --- | --- | --- | --- |
| | MIC MBC | | MIC MBC | | MIC MBC |
| Mode | 375 500 | Mode | 95 500 | Mode | 375 750 |
| Avg. | 260 581 | Avg. | 161 446 | Avg. | 323 666 |
| Mean | 260 581 | Mean | 161 446 | Mean | 323 666 |
| Median | 250 500 | Median | 95 500 | Median | 375 750 |
| Min. | 95 375 | Min. | 95 375 | Min. | 125 500 |
| Max. | 375 1000 | Max. | 250 500 | Max. | 375 1000 |

E. faecalis

| (all strains) | | (VAN R strains) | | (VAN S strains) | | (VAN S) model | |
| --- | --- | --- | --- | --- | --- | --- | --- |
| | MIC MBC | | MIC MBC | | MIC MBC | | MIC MBC |
| Mode | 375 500 | Mode | 250 500 | Mode | 250 500 | UK | 250 500 |
| Avg. | 310 606 | Avg. | 213 500 | Avg. | 289 566 | Switzerland | 375 500 |
| Mean | 310 606 | Mean | 213 500 | Mean | 289 566 | Germany | 375 750 |
| Median | 375 500 | Median | 250 500 | Median | 250 500 | | |
| Min. | 125 375 | Min. | 125 500 | Min. | 190 375 | | |
| Max. | 500 750 | Max. | 375 750 | Max. | 500 750 | | |

EXAMPLE 5

Two percent taurolidine solution was tested against various bacteria at 5×10⁴ CFU/well, according to *Manual of Clinical Microbiology,* 6th edition, P. R. Murray et al., pp. 1334–1335. The results are shown in Table 2.

TABLE 2

| Sample No. | Organism | MIC (mg/lt.) 24 h | MIC (mg/lt.) 48 h | MBC (mg/lt.) 24 h | VE[1] 30 |
| --- | --- | --- | --- | --- | --- |
| 1 | E. faecium | 190 | 250 | 500 | S |
| 2 | E. faecium | 375 | 375 | 500 | S |
| 3 | E. faecium | 190 | 250 | 500 | S |
| 4 | E. faecium | 250 | 250 | 375 | R |
| 5 | E. faecium | 250 | 250 | 375 | R |
| 6 | E. faecium | </=95 | 190 | 50 | R |
| 7 | E. faecium | 125 | 375 | 500 | S |
| 8 | E. faecium | </=95 | 190 | 500 | R |
| 9 | E. faecium | </=95 | 250 | 500 | R |
| 10 | E. faecium | 190 | 375 | 750 | S |
| 11 | Staph. app. | 190 | 250 | 375 | S |
| 12 | E. faecium | </=95 | 190 | 375 | S |
| 13 | E. faecium | 250 | 375 | 500 | S |
| 14 | E. faecium | 375 | 375 | 750 | S |
| 15 | E. faecium | 375 | 375 | 500 | S |
| 16 | E. faecium | 375 | 375 | 750 | S |
| 17 | E. faecium | 375 | 375 | 750 | S |
| 18 | E. faecium | 375 | 375 | 750 | S |
| 19 | E. faecium | 375 | 375 | 750 | S |
| 20 | E. faecium | 375 | 375 | 100 | S |
| 21 | E. faecalis | 375 | 375 | 500 | S |
| 22 | E. faecalis | 250 | 375 | 500 | S |
| 23 | E. faecalis | 250 | 375 | 500 | S |
| 24 | E. faecalis | 375 | 375 | 500 | S |
| 25 | E. faecalis | 375 | 375 | 500 | S |
| 26 | E. faecalis | 375 | 375 | 500 | S |
| 27 | E. faecalis | 250 | 250 | 500 | S |
| 28 | E. faecalis | 250 | 375 | 500 | S |
| 29 | E. faecalis | 190 | 250 | 500 | S |
| 30 | E. faecalis | 190 | 250 | 500 | S |
| 31 | E. faecalis | 375 | 375 | 500 | S |
| 32 | E. faecalis | 375 | 375 | 500 | S |
| 33 | E. faecalis | 250 | 250 | 750 | S |
| 34 | E. faecalis | 250 | 375 | 500 | S |
| 35 | E. faecalis | 250 | 250 | 500 | S |
| 36 | E. faecalis | 250 | 375 | 500 | R |
| 37 | E. faecalis | 250 | 250 | 500 | S |
| 38 | E. faecalis | 250 | 375 | 500 | R |
| 39 | E. faecalis | 250 | 375 | 500 | S |
| 40 | E. faecalis | 250 | 375 | 500 | S |
| 41 | E. faecalis | 190 | 190 | 500 | R |
| 42 | E. faecalis | 125 | 190 | 500 | R |
| 43 | E. faecalis | 250 | 375 | 750 | S |
| 44 | E. faecalis | 250 | 375 | 500 | R |
| 45 | E. faecalis | 250 | 250 | 500 | S |
| 46 | E. faecalis | 250 | 250 | 500 | S |
| 47 | E. faecalis | 250 | 250 | 500 | S |
| 48 | E. faecalis | 375 | 375 | 500 | S |
| 49 | E. faecalis | 250 | 375 | 500 | S |
| 50 | E. faecalis | 375 | 375 | 500 | S |
| 51 | E. faecalis | 375 | 500 | 750 | S |
| 52 | E. faecalis | 190 | 375 | 750 | S |
| 53 | E. faecalis | 375 | 375 | 750 | S |
| 54 | E. faecalis | 500 | 500 | 750 | S |
| 55 | E. faecalis | 375 | 500 | 750 | S |
| 56 | E. faecalis | 250 | 375 | 375 | S |
| 57 | E. faecalis | 375 | 500 | 750 | |

TABLE 2-continued

| Sample No. | Organism | MIC (mg/lt.) 24 h | MIC (mg/lt.) 48 h | MBC (mg/lt.) 24 h | VE[1] 30 |
|---|---|---|---|---|---|
| 58 | E. faecalis | 375 | 375 | 750 | |
| 59 | E. faecalis | 375 | 375 | 750 | |
| 60 | E. faecalis | 375 | 375 | 750 | |
| 61 | E. faecalis | 375 | 500 | 750 | |
| 62 | E. faecalis | 375 | 500 | 750 | |
| 63 | E. faecalis | 375 | 500 | 750 | |
| 64 | E. faecalis | 375 | 375 | 750 | |
| 65 | E. faecalis | 375 | 375 | 750 | |
| 66 | E. faecalis | 190 | 250 | 375 | |
| 67 | E. faecalis | 375 | 375 | 750 | |
| 68 | E. faecalis | 375 | 375 | 750 | |
| 69 | E. faecalis | 250 | 375 | 750 | |
| 70 | E. faecalis | 375 | 500 | 750 | |
| 71 | E. faecalis | 375 | 500 | 750 | |
| 72 | E. faecalis | 375 | 375 | 750 | |
| 73 | E. faecalis | 375 | 500 | 750 | |
| 74 | E. faecalis | 375 | 375 | 750 | |

[1]VE30: Resistance to Vancomycin (30 µg/Disc)
R = Resistant to Vancomycin (VE)
S = Sensitive to VE

I claim:

1. A method of treating a microbial infection within a patient's intestine, selected from the group consisting of an intestinal bacterial infection, an intestinal fungal infection and a combination thereof, comprising:
    orally administering so as to introduce into a patient's gut a non-antibiotic antimicrobial medicament which is microbial cell wall constituent-inactivating by cell wall cross-linking, endotoxin non-releasing, and/or exotoxin-inactivating, and combinations thereof, so as to treat said microbial intestinal infection of said patient.

2. The method of claim 1 wherein said antimicrobial medicament is administered in a tablet, capsule, liquid, suspension or suppository.

3. The method of claim 1 wherein said antimicrobial medicament is administered so that said medicament is continuously present in said gut over a course of the treatment.

4. The method of claim 1, further including intravenous administration in conjunction with the oral administration thereof.

5. The method of claim 1 wherein the microbial infection is by an antibiotic-resistant microorganism.

6. The method of claim 1 wherein the microbial infection is by a gram negative bacterium or a gram positive bacterium.

7. The method of claim 1 wherein the microbial infection is by Enterococci.

8. The method of claim 7 wherein the Enterococci are antibiotic-resistant Enterococci.

9. The method of claim 8 wherein the microbial infection is by vancomycin-resistant *Enterococcus faecalis* (VRE).

10. The method of claim 1 wherein the microbial infection is by Staphylococci.

11. The method of claim 10 wherein the Staphylococci are antibiotic-resistant.

12. The method of claim 11 wherein the microbial infection is by methicillin-resistant *Staphylococcus aureus* (MRSA).

13. The method of claim 1 wherein the microbial infection is by antibiotic-resistant *Enterococcus faecium*.

14. The method of claim 1 wherein the antimicrobial medicament is selected from the group consisting of taurolidine, taurultam and a combination thereof.

15. A method of treating an intestinal bacterial infection, an intestinal fungal infection or a combination thereof within a patient's intestine, absent infections due to surgery and injury, comprising orally administering so as to introduce into a patient's gut a medicament comprising taurolidine, taurultam or a combination thereof, so as to treat said intestinal infection of said patient.

16. The method of claim 15 wherein said infection is an infection by vancomycin-resistant *Enterococcus faecalis* (VRE) or methicillin-resistant *Staphylococcus aureus* (MRSA).

17. The method of claim 1 wherein the microbial intestinal infection causes diarrhea in the patient, and wherein said medicament is administered to said patient so as to treat said diarrhea.

18. The method of claim 15 wherein the microbial intestinal infection causes diarrhea in the patient, and wherein said medicament is administered to said patient so as to treat said diarrhea.

* * * * *

UNITED STATES PATENT AND TRADEMARK OFFICE
CERTIFICATE OF CORRECTION

PATENT NO. : 5,972,933

DATED : October 26, 1999

INVENTOR(S) : Rolf W. PFIRRMANN

It is certified that error appears in the above-identified patent and that said Letters Patent is hereby corrected as shown below:

COLUMN 6, LINE 39,

"Prom" should be --From--.

COLUMN 9, TABLE 2,

Sample 20, the MBC should be changed from "100" to --1000--

Signed and Sealed this

Fifth Day of December, 2000

Attest:

Q. TODD DICKINSON

Attesting Officer

Director of Patents and Trademarks